(12) United States Patent
Norris et al.

(10) Patent No.: US 8,116,839 B1
(45) Date of Patent: Feb. 14, 2012

(54) SYSTEM FOR DETECTING POTENTIAL PROBE MALFUNCTION CONDITIONS IN A PULSE OXIMETER

(75) Inventors: Mark A. Norris, Louisville, CO (US); Donald W. Heckel, Thornton, CO (US)

(73) Assignee: General Electric Company, Schenectady, NY (US)

( * ) Notice: Subject to any disclaimer, the term of this patent is extended or adjusted under 35 U.S.C. 154(b) by 1609 days.

(21) Appl. No.: 11/363,553

(22) Filed: Feb. 27, 2006

Related U.S. Application Data

(60) Provisional application No. 60/656,197, filed on Feb. 25, 2005.

(51) Int. Cl.
*A61B 5/1455* (2006.01)

(52) U.S. Cl. ........................ 600/323; 600/310

(58) Field of Classification Search ........... 600/309–344
See application file for complete search history.

(56) References Cited

U.S. PATENT DOCUMENTS

| | | | |
|---|---|---|---|
| 3,704,706 A | 12/1972 | Herczfeld et al. | |
| 4,306,567 A | 12/1981 | Krasner | |
| 4,379,460 A | 4/1983 | Judell | |
| 4,404,974 A | 9/1983 | Titus | |
| 4,510,944 A | 4/1985 | Porges | 128/687 |
| 4,765,340 A | 8/1988 | Sakai et al. | |
| 4,777,960 A | 10/1988 | Berger et al. | 128/706 |
| 4,781,201 A | 11/1988 | Wright et al. | |
| 4,813,427 A | 3/1989 | Schlaefke et al. | 128/671 |
| 4,860,759 A | 8/1989 | Kahn et al. | 128/668 |
| 4,863,265 A | 9/1989 | Flower et al. | |
| 4,869,254 A | 9/1989 | Stone et al. | |
| 4,884,578 A | 12/1989 | Morgenstern | |
| 4,899,760 A | 2/1990 | Jaeb et al. | 128/696 |
| 4,911,167 A | 3/1990 | Corenman et al. | |
| 4,930,517 A | 6/1990 | Cohen et al. | 128/671 |
| 4,958,638 A | 9/1990 | Sharpe et al. | |
| 4,960,129 A | 10/1990 | DePaola et al. | 128/695 |
| 4,972,842 A | 11/1990 | Korten et al. | 128/716 |
| 5,033,472 A | 7/1991 | Sato et al. | 128/691 |
| 5,078,136 A | 1/1992 | Stone et al. | |
| 5,111,817 A | 5/1992 | Clark et al. | |
| 5,170,794 A | 12/1992 | Reiche | |
| 5,273,036 A | 12/1993 | Kronberg et al. | 128/633 |
| 5,368,224 A | 11/1994 | Richardson et al. | |
| 5,385,144 A | 1/1995 | Yamanishi et al. | |
| 5,396,893 A | 3/1995 | Oberg et al. | |
| 5,423,322 A | 6/1995 | Clark et al. | |

(Continued)

FOREIGN PATENT DOCUMENTS

AT    WO0125802    4/2001

*Primary Examiner* — Eric Winakur
*Assistant Examiner* — Marjan Fardanesh
(74) *Attorney, Agent, or Firm* — Marsh Fischmann & Breyfogle LLP

(57) ABSTRACT

An initialization module in a pulse oximeter accommodates a variety of different probes and a variety of operating parameters as well as providing for interrogation of various probe circuits for detection of probe faults. Probe fault detection for the red and infrared LED circuits of the probe is implemented using an adaptive algorithm that is dependent on the drive settings or signals applied to the LED circuits. A configurable circuit is used to provide multiple initialization values relating to a calibration circuit of the probe for improved fault detection. Additionally, potential faults with respect to the photodetector circuit of a probe are identified based on monitoring drawn by an output by the photodetector.

14 Claims, 11 Drawing Sheets

U.S. PATENT DOCUMENTS

| | | |
|---|---|---|
| 5,431,159 A | 7/1995 | Baker et al. |
| 5,482,036 A | 1/1996 | Diab et al. |
| 5,490,505 A | 2/1996 | Diab et al. |
| 5,511,553 A | 4/1996 | Segalowitz .................. 128/696 |
| 5,553,615 A | 9/1996 | Carim et al. |
| 5,555,882 A | 9/1996 | Richardson et al. |
| 5,575,284 A | 11/1996 | Athan et al. |
| 5,623,933 A | 4/1997 | Amano et al. |
| 5,755,229 A | 5/1998 | Amano et al. |
| 5,766,127 A | 6/1998 | Pologe et al. |
| 5,776,071 A | 7/1998 | Inukai et al. |
| 5,783,821 A * | 7/1998 | Costello, Jr. .............. 250/252.1 |
| 5,830,137 A | 11/1998 | Scharf |
| 5,853,364 A | 12/1998 | Baker, Jr. et al. |
| 5,862,805 A | 1/1999 | Nitzan |
| 5,865,167 A | 2/1999 | Godik |
| 5,865,756 A | 2/1999 | Peel, III |
| 5,885,213 A | 3/1999 | Richardson et al. |
| 5,902,235 A | 5/1999 | Lewis et al. |
| 5,919,134 A | 7/1999 | Diab |
| 5,931,779 A | 8/1999 | Arakaki et al. |
| 5,934,277 A | 8/1999 | Mortz |
| 5,954,644 A | 9/1999 | Dettling et al. |
| 5,971,930 A | 10/1999 | Elghazzawi |
| 5,980,463 A | 11/1999 | Brockway et al. ............ 600/485 |
| 5,997,482 A | 12/1999 | Vaschillo et al. |
| 6,002,952 A | 12/1999 | Diab et al. |
| 6,011,985 A | 1/2000 | Athan et al. |
| 6,027,455 A | 2/2000 | Inukai et al. .................. 600/490 |
| 6,028,311 A | 2/2000 | Sodickson et al. |
| 6,064,910 A | 5/2000 | Andersson et al. |
| 6,067,462 A | 5/2000 | Diab et al. |
| 6,081,742 A | 6/2000 | Amano et al. ............... 600/513 |
| 6,083,172 A | 7/2000 | Baker, Jr. et al. |
| 6,094,592 A | 7/2000 | Yorkey et al. |
| 6,099,481 A | 8/2000 | Daniels et al. ............... 600/538 |
| 6,129,675 A | 10/2000 | Jay ................................ 600/485 |
| 6,155,992 A | 12/2000 | Henning et al. ............. 600/583 |
| 6,263,222 B1 | 7/2001 | Diab et al. |
| 6,393,311 B1 | 5/2002 | Edgar, Jr. et al. |
| 6,480,733 B1 | 11/2002 | Turcott ......................... 600/516 |
| 6,519,486 B1 | 2/2003 | Edgar, Jr. et al. |
| 6,650,917 B2 | 11/2003 | Diab et al. |
| 6,668,183 B2 * | 12/2003 | Hicks et al. .................. 600/331 |
| 6,810,277 B2 | 10/2004 | Edgar, Jr. et al. |
| 2004/0039273 A1 | 2/2004 | Terry |
| 2006/0206020 A1 * | 9/2006 | Liao et al. .................... 600/323 |

\* cited by examiner

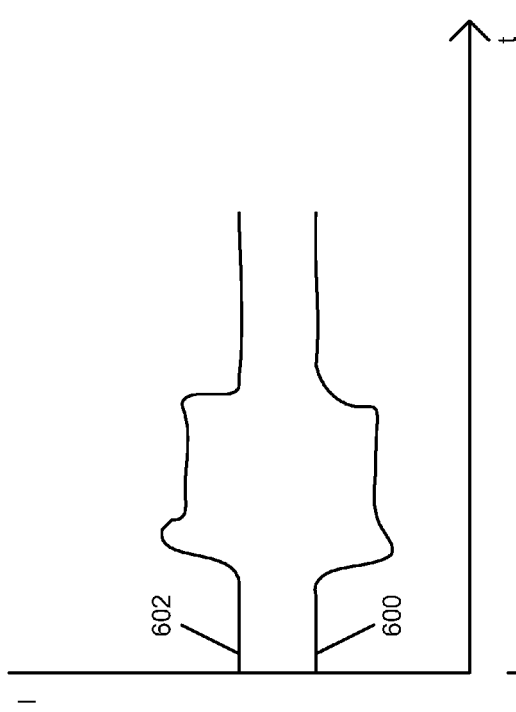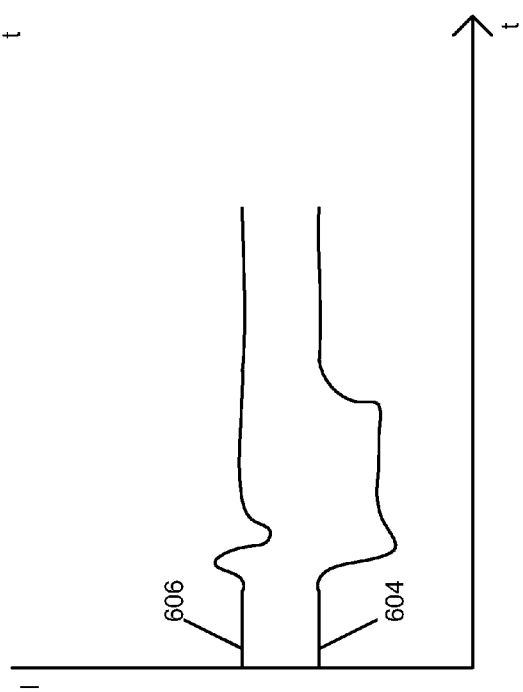

SYSTEM FOR DETECTING POTENTIAL PROBE MALFUNCTION CONDITIONS IN A PULSE OXIMETER

CROSS REFERENCE TO RELATED APPLICATION

The present application claims priority under 35 U.S.C. §119 to U.S. Provisional Application No. 60/656,197 entitled: "System for Detecting Potential Probe Malfunction Conditions in a Pulse Oximeter" and having a filing date of Feb. 25, 2005, the entire contents of which are incorporated by reference herein.

FIELD OF THE INVENTION

The present invention relates in general to pulse oximetry and, in particular, to obtaining probe initialization information including information for detecting potential malfunction conditions, such as short circuits or open circuits, in a pulse oximeter probe selected for potential use in connection with a pulse oximeter monitor.

BACKGROUND OF THE INVENTION

Pulse oximetry systems generally include probes for attachment to an appendage of a patient for transmitting red and infrared signals to the patient's appendage and detecting the signals transmitted through or reflected from the patient's appendage. A monitor usually drives the probes and processes the probe signals to determine, among other things, the oxygenation of the patient's blood and the patient's pulse rate. Probe cabling typically interconnects the probe to a monitor to define the pulse oximetry system. Pulse oximetry probes are generally disposable or single-use products. By contrast, the monitors are intended for long-term use. Thus, many different probes are connected to a monitor over time.

In order to ensure functioning of the pulse oximetry system as intended, when a particular probe is interconnected, the monitor generally implements an initialization process. Initialization may involve a number of processes including a shorts and opens routine, probe family identification, qualification and calibration.

The shorts and opens routine is intended to identify potential malfunction conditions, such as short or open circuits, in the probe. In this regard, the probe typically includes circuitry for driving multiple LEDs—e.g., a red LED and an infrared LED—a detector circuit, and certain probe identification and calibration components, as will be described below.

In connection with one exemplary conventional shorts and opens routine, the voltage drop across two probe pins associated with the infrared LED is detected periodically. The measured voltage drop is compared to low and high threshold values to ensure that the measured voltage drop is within a proper operating range. In this manner, potentially dangerous probe conditions can be identified so as to better ensure patent safety. If the measured voltage drop is not within the proper operating range, the probe drive is disabled.

In connection with the probe family identification process, in the noted conventional oximeter, a signal applied across two probe pins may be used to determine whether a family identification diode is present. The presence or absence of this diode enables the monitor to set the probe family type, e.g., to determine whether the probe is a finger probe or an ear probe. This information is then used to operate the monitor. Both the shorts and opens analysis and the family identification analysis may be performed periodically, e.g., every two seconds during oximeter operation.

In addition to these processes, initialization may involve probe qualification and calibration. Qualification relates to verifying that the probe is a type of probe supported or authorized for use by the monitor and that the probe is otherwise functioning properly, i.e., that the probe may be used for patient monitoring or that full functionality may be implemented. This decision is binary in nature, i.e., involves a single determination as between two states. That is, the probe is either "qualified" for use in the system or "disqualified". The result of a disqualification determination is generally that the probe drive components of the monitor are disabled to prevent any use of the probe in the system for patient monitoring, or certain functionality is disabled.

Calibration relates to adapting the system to the particular characteristics of the attached probe. In this regard, as noted above, each probe generally includes at least a red LED and an infrared LED. The center wavelengths of these LEDs vary from probe to probe. During a calibration process, the values of these wavelengths are identified. These values can then be used to customize the algorithms used for determining blood oxygen saturation, e.g., by appropriate selection of the coefficients of a series of algorithm terms. Calibration thus involves quantifying probe characteristics relative to an expected range of values.

More specifically, certain conventional systems interrogate a calibration resistor, Rcal, of the probe used to encode the wavelength values of the red and infrared LEDs During manufacturing, the wavelength values of these LEDs are determined. These values are encoded by the resistance value of the Rcal resistor which is wired across two pins of the probe. That is, each supported combination of red and infrared wavelengths is associated with an Rcal value and associated relationships are stored for use by the monitor processing unit. During initialization, a known potential or signal is applied across the Rcal pins and a value related to the Rcal resistor, such as a voltage drop, is determined. In turn, this value is used to select the proper coefficients for the corresponding red and infrared wavelengths.

It will be appreciated that proper functioning of a pulse oximeter depends on successful completion and accurate interpretation of these initialization processes.

SUMMARY OF THE INVENTION

It has been recognized that certain initialization processes as discussed above are complicated by operational variations and are compromised due to limited interrogation of probe circuitry for initialization. Such operational variations include equipment and operating parameter variations. With respect to equipment variations, some manufacturers desire to accommodate a variety of probes including probes of different families from the same manufacturer and probes of different manufacturers. These probes may or may not be designed for broad compatibility with available monitors. Regarding operating parameter variations, the sources or LEDs may be driven to transmit signals of varying transmitted intensities due to variations in probe location, patient skin pigmentation and other factors. As a result of these operational variations, conventional initialization measurements may be inadequate to yield the desired initialization information in some contexts.

Moreover, certain conventional initialization processes, including certain shorts and opens routines, provide limited initialization information. For example, as noted above, typical probes include a variety of circuitry including multiple LED circuits, calibration circuits such as so-called Rcal circuits, and detector circuits. All of these circuits are subject to wear and potential malfunctions. Indeed, probes are often intended for short-term use and are designed for low cost construction. Yet, certain conventional shorts and opens routines diagnose only particular circuits such as that associated with an IR LED. While such routines have significant value in detecting potential malfunctions, they may miss potential malfunctions affecting other probe circuits.

The present invention provides improved initialization including initialization adapted to properly handle a variety of operational variations. In this regard, the present invention allows for initialization processes that accommodate a variety of different probes that may provide different responses to initialization interrogation signals, thereby allowing for proper initialization and avoiding erroneous invalidation of authorized and properly functioning probes or erroneous validation or calibration. The invention also accommodates a variety of operating parameters while allowing for obtainment of useful initialization information. Moreover, the invention provides for improved interrogation of various probe circuits for better identification of potential malfunctions or improved initialization information.

In accordance with one aspect of the present invention, a method and apparatus ("utility") are provided for drive-dependent initialization. The utility involves logic for determining probe initialization information as a function of one or more parameters of signals applied to probes. For example, the initialization information may relate to valid values of probe elements or encoded calibration information. This initialization information may be a function of drive parameters such as drive voltage, current or other drive parameters. The utility further involves obtaining parameter information for a particular signal applied to a particular probe and using the parameter information, together with the logic, to control operation of the pulse oximeter in connection with the probe. For example, the pulse oximeter may be controlled to prevent operation with the probe due to an indication of potential malfunction or indication that the probe is potentially unauthorized for use with the pulse oximeter, or the oximeter may be controlled to obtain appropriate calibration or other information. In this manner, an initialization process can accommodate varying operating parameters.

In accordance with another aspect of the present invention, a utility is provided for validating a probe on a drive-dependent basis. The utility involves: obtaining information regarding drive parameters for driving the probe; based on such drive information, obtaining drive-dependent valid operating information relating to one or more components of the probe (e.g., for a component(s) of for the probe considered as a whole); obtaining a measured operating parameter relating to the one or more probe components; comparing the measured parameter to the drive dependent operating parameter, and operating the pulse oximetry based on the comparison. For example, a conventional shorts and opens routine may define a range of acceptable voltage drops for a probe component. In accordance with the present invention, such a range may be defined as an adaptive window of values that moves depending on the drive voltage and/or current. An associated methodology involves selecting a drive setting and operating the pulse oximeter such that the probe is validated in a manner that is dependent on the setting (e.g., as detected directly or detected based on the resulting drive signal).

In accordance with a further aspect of the invention, a utility is provided for obtaining information regarding a photoactive element of an oximeter probe such as a photodetector. The utility involves providing a photoactive element for generating electrical signals responsive to optical signals incident thereon; applying an optical signal to the photoactive element and detecting the resulting electrical signal. For example, the optical signal may be a dedicated signal of a separate initialization process or may be a signal used for measuring a physiological parameter of a patient. The detected electrical signal is used to obtain information regarding the photoactive element for use in controlling operation of the pulse oximeter in connection with the probe including the photoactive element. In this regard, the information regarding the photoactive element may be used to verify that the element is functioning properly, to identify the element/probe, or for calibration purposes. In one implementation, the detected output electrical signal from the element is compared with a corresponding input signal drawn by the element to verify proper functioning of the element. In this manner, for example, opens or shorts affecting the photoactive element can be detected.

In accordance with yet another aspect of the present invention, a utility is provided that allows for reconfiguration of a circuit for interfacing with a portion of an oximeter probe, e.g., a circuit of the probe or a disposable portion of the probe. The utility involves a circuit configurable between first and second circuit configurations and a port for removably interconnecting the oximeter probe portion into the circuit. For example, the circuit may be disposed in a monitor or other signal processing unit and/or in a cable or other interface between a processing unit and a probe. The port may include a standardized interface, such as a socket, by which probes may be successively interconnected to the circuit. The circuit is reconfigurable such that at least one circuit element, e.g., a passive element such as a resistor, may be selectively isolated from or integrated into the circuit. In this manner, the circuit can be reconfigured so as to enable two measurements for internal circuit calibration or improved accuracy or certainty in obtaining initialization information from the probe. In one implementation, the circuit is operative for reading calibration information from the probe and/or for detecting potential faults in an associated circuit.

In accordance with another aspect of the present invention, a reconfigurable circuit is used for obtaining initialization information from an oximeter probe. The utility involves providing a circuit for obtaining initialization information for a pulse oximetry procedure, configuring the circuit in a first configuration to obtain a first output responsive to a first interrogation signal, configuring the circuit in a second configuration to obtain a second output responsive to a second interrogation signal, and using the first and second outputs to obtain the initialization information. The circuit, or at least the reconfigurable portion thereof, may be disposed in a probe, a processing unit, or an interface therebetween. The initialization information may include, for example, calibration information, probe identification information and/or information for use in determining the presence or absence of a probe fault condition.

In accordance with another aspect of the present invention, a pulse oximeter is operated to identify any potential malfunctions or faults with respect to each of multiple components of a single probe. An associated utility involves executing a first process for determining the presence or absence of a potential fault condition with respect to a first circuit of an oximeter probe, executing a second process for determining the presence or absence of a potential fault condition with respect to a second circuit, at least partially different than the first circuit, of the probe, and controlling operation of the oximeter based on the results of the first and second processes. For example, separate shorts and opens routines may be run with respect to any two of a first source circuit, a second source circuit, a probe identification circuit, a probe calibration circuit and a photodetector circuit. In this manner, improved identification of probe faults is enabled.

BRIEF DESCRIPTION OF THE DRAWINGS

For a more complete understanding of the present invention and further advantages thereof, reference is now made to the following detailed description, taken in conjunction with the drawings, in which:

FIGS. 6A-6B illustrate examples of signals that may be detected by the circuit of FIG. 5;

DETAILED DESCRIPTION

In the following description, the invention is set forth in the context of a particular pulse oximetry system—including specific monitor hardware and software and a specific probe—implementing specific initialization processes with a focus on shorts and opens (probe fault) routines. It should be appreciated, however, that the particular pulse oximetry system can vary in accordance with the present invention. Indeed, one objective of the present invention is to accommodate a variety of probes and pulse oximetry environments while reliably and accurately obtaining the desired initialization information. Accordingly, the following description should be understood as exemplifying the invention and not by way of limitation.

Figure 1:
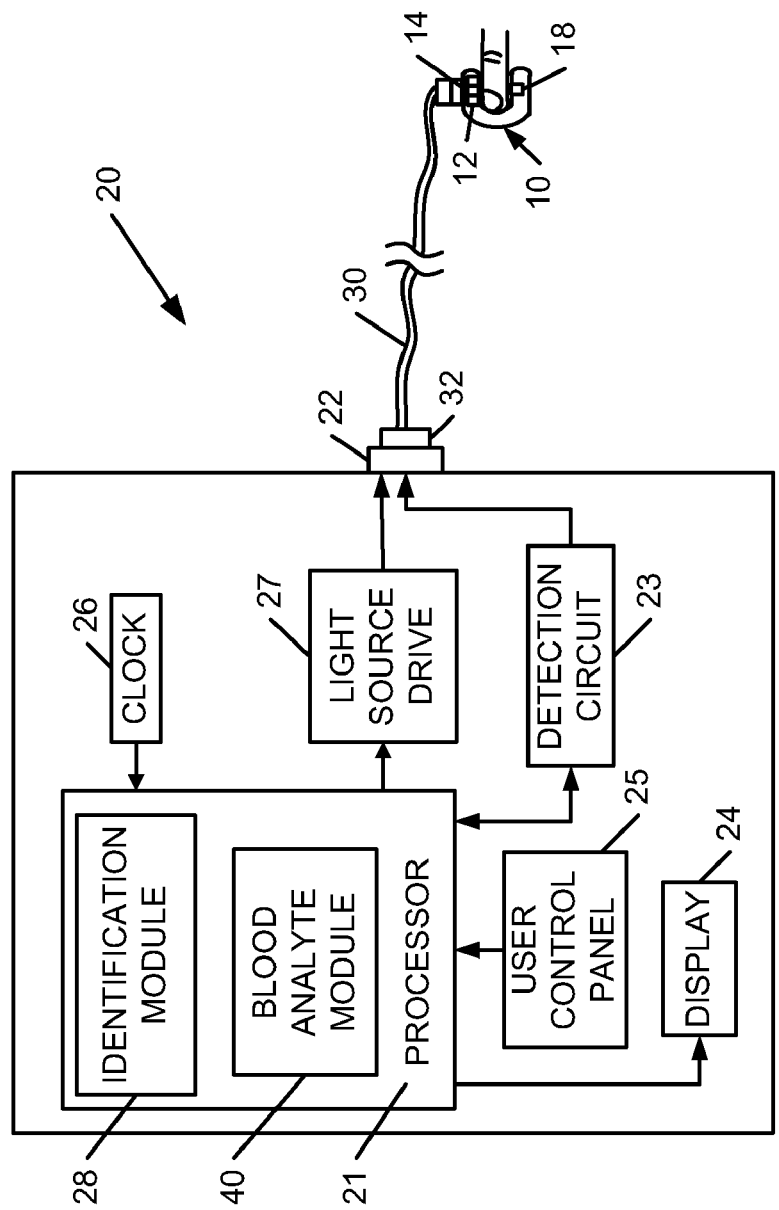
FIG. 1 illustrates one embodiment of a photoplethysmographic system application of the present invention.
Figure 2:
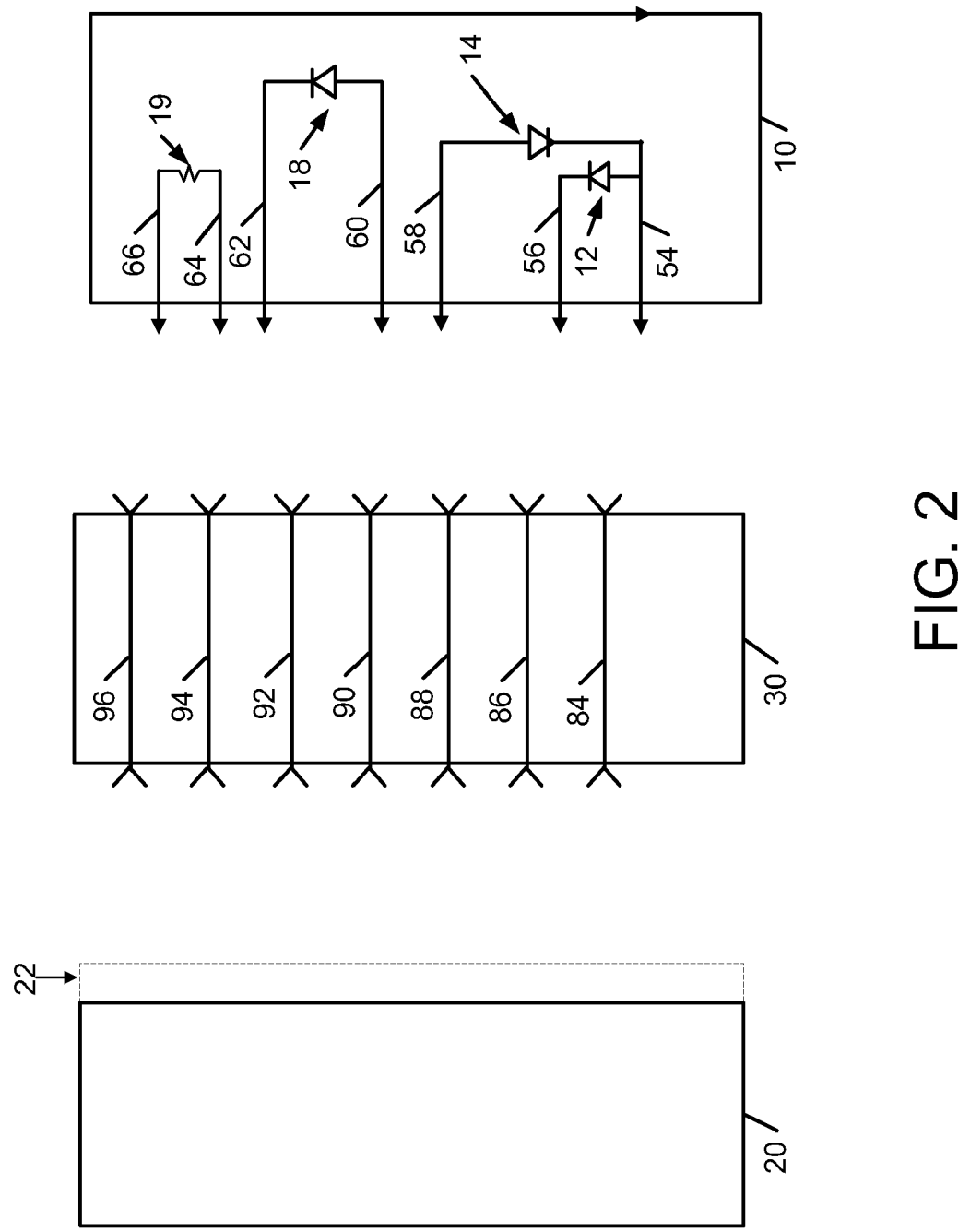
FIG. 2 illustrates sensor, cable and monitor interconnections for the application of FIG. 1.

FIGS. 1 and 2 illustrate a photoplethysmographic system of the present invention. As will be described in detail below, the illustrated system is operative to identify and selectively employ sensors, including sensors that are compatible with other systems, to obtain calibration information from the sensor, to execute probe fault routines, and to otherwise obtain initialization information.

In the system of FIG. 1, a photoplethysmographic monitor 20 is shown interconnected to a probe 10 via a cable 30. For purposes of the present description, probe 10 may be of a type that may be compatible with a number of different monitors, which may vary in type. Such different monitors may include differing electrical configurations, e.g., of their respective cable interconnection ports and/or corresponding different signal processing and parameter calculation modules. Often, the sensors are disposable or single-use products. By contrast, the monitors are intended for long-term use. Thus, many different sensors are connected to a monitor over time. As described below, the illustrated monitor 20 to be compatible with a variety of sensors, including a variety of sensors that are designed for use with a particular monitor or monitors.

In order to utilize a variety of sensors with a particular monitor, it is generally necessary to identify the particular characteristics of an attached sensor as well as to implement a variety of other processes that may vary from sensor to sensor. That is, to ensure functioning of the photoplethysmographic system as intended, when a sensor is interconnected, the monitor generally implements an initialization process. Initialization may involve multiple separate analyses of the sensor. As noted above, these processes may include, among other things, probe identification, family identification, qualification, calibration and fault detection. Some of these processes may overlap. For example, a value read from the probe may identify a sensor or sensor family, as well as verifying qualification and indicating the absence of a fault in the relevant circuit.

As shown in FIG. 1, the monitor 20 may be designed with port 22 including a socket or sockets, with appropriate pin interfaces, for driving two light sources 12 and 14 of the probe 10. Alternatively or additionally, the port 22 may allow for driving more than two sources.

In the system shown in FIG. 1, the monitor 20 includes a processor 21 and a clock 26 that may operate to trigger light source drive 27 to transmit drive signals via cable 30 to the probe 10. In cases where probe 10 is determined to be compatible with the monitor 20 and functional, a drive signal may be provided to pulse the light sources 12 and/or 14 in accordance with a predetermined multiplexing scheme (e.g. a time-division, frequency-division or code-division multiplexing scheme) causing sources 12 and/or 14 to emit light at different center wavelengths for which the monitor 20 has been preset or may be calibrated for in operation.

By way of example, in the system of FIG. 1, light sources 12 and 14 may be selectively pulsed to illuminate a patient tissue under test with red and infrared light at first and second center wavelengths, respectively. Although a finger probe 10 is illustrated, it will be appreciated that an ear lobe, nasal septum or foot probe, or probes for other body locations (e.g., reflective probes) may be utilized in accordance with the present invention. Upon tissue illumination, a light detector 18 of the probe 10 may detect the intensity of light transmitted by the tissue under test and provide a corresponding output signal. In turn, the monitor 20 may process the detector output signal utilizing stored values, or algorithms preset in relation to the center wavelengths of the light sources 12 and/or 14 of probe 10.

In the system of FIG. 1, the detector output signal of the probe 10 may be transmitted by cable 30 for conversion/conditioning by a detection circuit 23, and processing by a processor 21. For example, detection circuit 23 may comprise amplification, filtering and analog-to-digital conversion componentry, as well as other componentry for conditioning the signal. In this regard, the analog-to-digital componentry of the illustrated system preferably samples the detector signal at a rate which is significantly greater than required to satisfy the Nyquist sampling criteria. For example, the illustrated circuit 23 may include an oversampling A/D converter that has a frequency of, for example, 40-50 kHz, which, depending on the specific source frequencies employed and multiplexing scheme, may sample the detector signal many times, e.g., 20 or more times, in a time period corresponding to an "on" or high energy portion of the source cycle. Detection circuit 23 or processor 21 also may be adapted to demultiplex detector signals (e.g. in corresponding relation to a given light source multiplexing scheme) so that signal portions corresponding with the light sources 12 and/or 14 may be separately processed as well as to demodulate the signals to as to separate the physiological signal from the carrier waveform.

In conjunction with such processing, probe 10 may be identified to confirm compatibility and functionality and to extract other initialization information. Additionally, one or more physiologic parameter measurements may be determined using the detector output signal and output to a user via monitor display 24. By way of example, the monitor 20 may utilize the detector output signal to determine $SpO_2$ and pulse/heart rate values and to display a pulsatile waveform. In this regard, the monitor 20 may include a blood analyte measurement module 28 for providing blood analyte information (e.g., blood oxygen saturation and pulse rate values), and other modules for providing other photoplethysmographic measurement information derivable from the data received from the sensor and/or stored in a data buffer.

In the later regard, blood analyte measurement module 28 may access one or more values to compute differential absorption data sets (e.g., differential infrared light and differential red light data sets) from which blood analyte values may be determined utilizing stored values, or algorithms, which use the center wavelengths of the light sources of a given compatible probe, e.g. light sources 12 and 14 of the probe 10. In this regard, blood analyte computation measurement module 28 may incorporate known processes, including such as those taught by U.S. Pat. Nos. 5,503,148; 5,842,979; 5,891,024 and 5,934,277 which are incorporated herein by reference.

Referring now to FIG. 2, the illustrated light sources 12 and 14 of probe 10 may be associated with sensor terminals 54, 56 and 58 to provide an electrical interface to the monitor 20. The probe 10 further includes a detector 18 associated with sensor terminals 60 and 62 and an identification and/or calibration element (e.g., a bin or Rcal resistor) 19 associated with sensor terminals 64 and 66. As shown, the cable 30 interconnecting the probe 10 to the monitor 20 utilizes multiple individual conductor lines, 84-96 to interconnect the sensor terminals 54-66 on the probe 10 to the pins within the port 22. It will be appreciated that a different number of terminals, lines and pins associated with different probe circuitry may be utilized in accordance with the present invention and appropriate adaptors or other components may be provided to enable the monitor 20 and/or cable 30 to interface with a variety of probes in this regard. In this regard, each component 12, 14, 18 and 19 of the probe 10 may be individually interrogated to obtain initialization information, e.g., tested for probe-fault conditions. That is, for example, at least one interrogation signal may be applied across each probe component 12, 14, 18 and 19 to determine if that component is functioning properly. Though use of individual conductors allows for increased flexibility in operation, alternate interconnecting schemes, for example, where two or more probe components share a conductor, are possible in accordance with the present invention.

In use, any of the probe components 12, 14, 18 and 19 may be interrogated to obtain initialization information, e.g., may be probe-fault tested to determine if the probe 10 is functional. For example, an interrogation signal may be applied across one or more of the sensor components 12, 14, 18 and 19 in order to obtain a "test signature" for a given component. This test signature may then be compared to a "reference signature" for sensor identification, calibration, probe-fault and other initialization purposes. Alternatively or additionally, such initialization information from the probe 10 may be used to obtain calibration or other information from storage, e.g., from a look-up table. Such signatures may be represented, for example, as individual values, multiple values or waveforms/waveform parameters. For purposes of applying an interrogation signal, the processor 20, drive source 27 and/or clock 26 of the monitor 20 may be operated to transmit an appropriate signal across the component to be analyzed. In this regard, a test signature for a known interrogation signal may be obtained for a given probe component (e.g., elements 12, 14, 18 and 19).

The monitor 20 of FIG. 1 may include one or more data storage buffers for use in processing the initialization information received in response to the interrogation signals applied to the sensor components 12, 14, 18 and 19. For instance, the monitor 20 may include an initialization module 40 for use in conjunction with the present invention. Generally, this module 40 allows for the identification of compatible probes, for retrieving calibration information, for determining the proper functionality of those sensors 10 and for otherwise obtaining and processing initialization information. Numerous sensor identification and calibration schemes are possible. Such schemes include those described in U.S. Pat. Nos. 4,700,708 and 6,668,183 the contents of which are incorporated herein by reference.

Probe-fault detection in the illustrated system involves a specific test for each probe component 12, 14, 18 and 19 of interest. In this manner, improved fault detection is provided in relation to conventional fault detection processes. Furthermore, each type of sensor component (e.g., LEDs, photodetectors, identification calibration element) may require a different type of test and may provide different identification challenges. In order to address the challenges for different types of sensor components the following discussion is directed to probe-fault detection for identification/calibration elements, photodetectors and light sources. Of note, any or all of the following probe-fault detection methodologies may be incorporated into a single system and fault detection for other probe components may be provided.

Identification/Calibration Circuit Fault Detection

In many instances, the identification/calibration element 19 of a given probe 10 includes at least a first resistor. However, it will be appreciated that the element 19 may include various combinations of electrical components between the probe terminals 64 and 66. Accordingly, different test signals may be produced in relation to different applied interrogation signals. For instance, in some embodiments, the element 19 may be operative to provide first and second outputs when first and second signals of opposite polarities are applied across the probe terminals 64 and 66. One example of such a system is provided in U.S. Pat. No. 6,668,183, which is incorporated herein by reference.

In cases where the element 19 includes at least one resistor, a particular probe identification and calibration problem may arise. Specifically, cases may exist where a problem with the identification/calibration value, sensor wiring and/or the interconnecting cable may result in an incorrect test signature. In particular, one or more problems with the associated "circuit" may result in a test signature that while incorrect correlates to a legal value. In such a case, the monitor 20 may, for example, fail to properly identify an incompatible or unauthorized probe, may select incorrect LED center wavelength values for calibration purposes or may otherwise erroneously process the initialization information. In this regard, is desirable to confirm that the test signature from the identification/calibration circuit is valid.

Figure 3A:
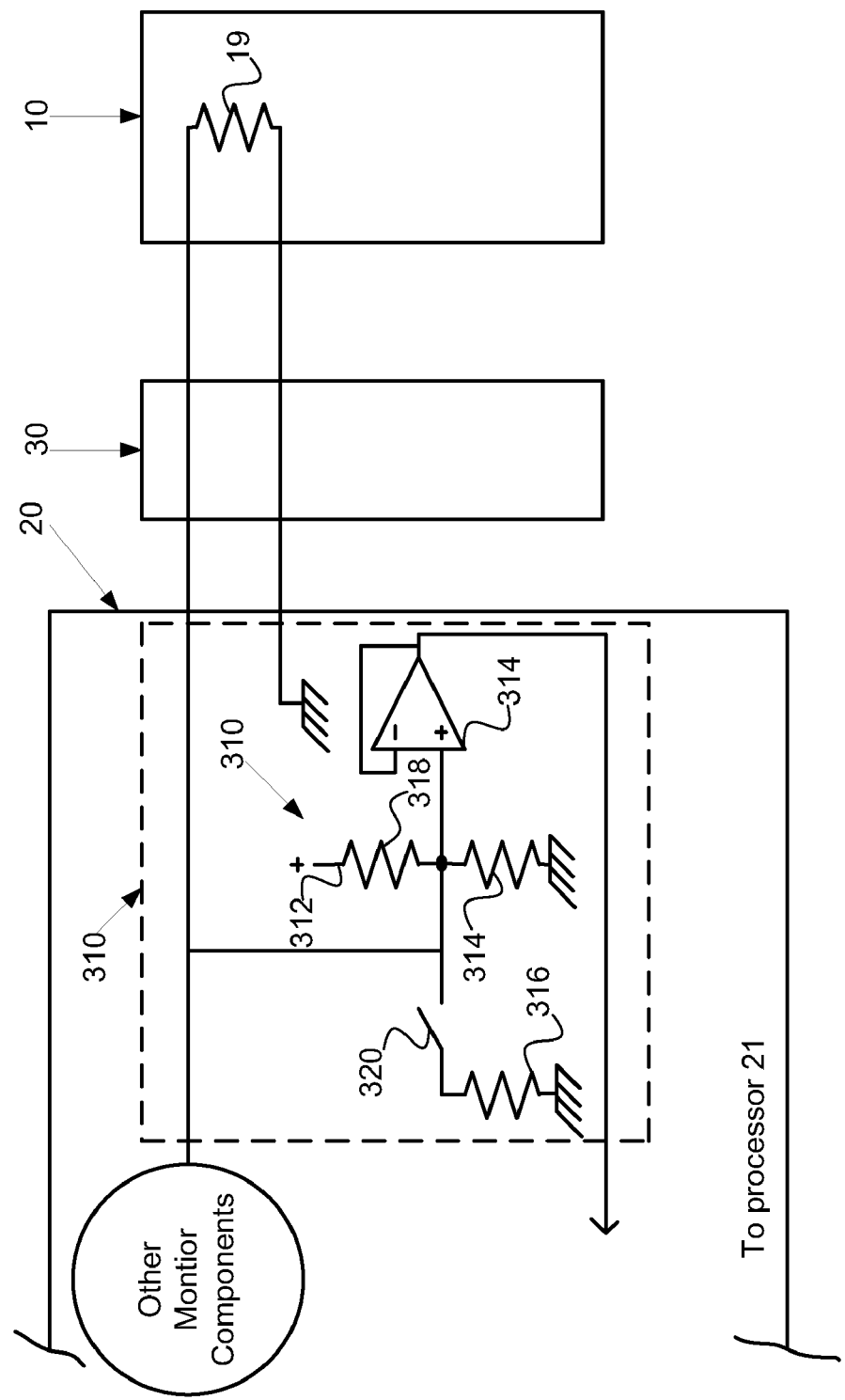
FIGS. 3A and 3B illustrates an one embodiment of an identification/calibration circuit in first and second configurations, respectively, for use in the system of FIG. 1.
Figure 3B:
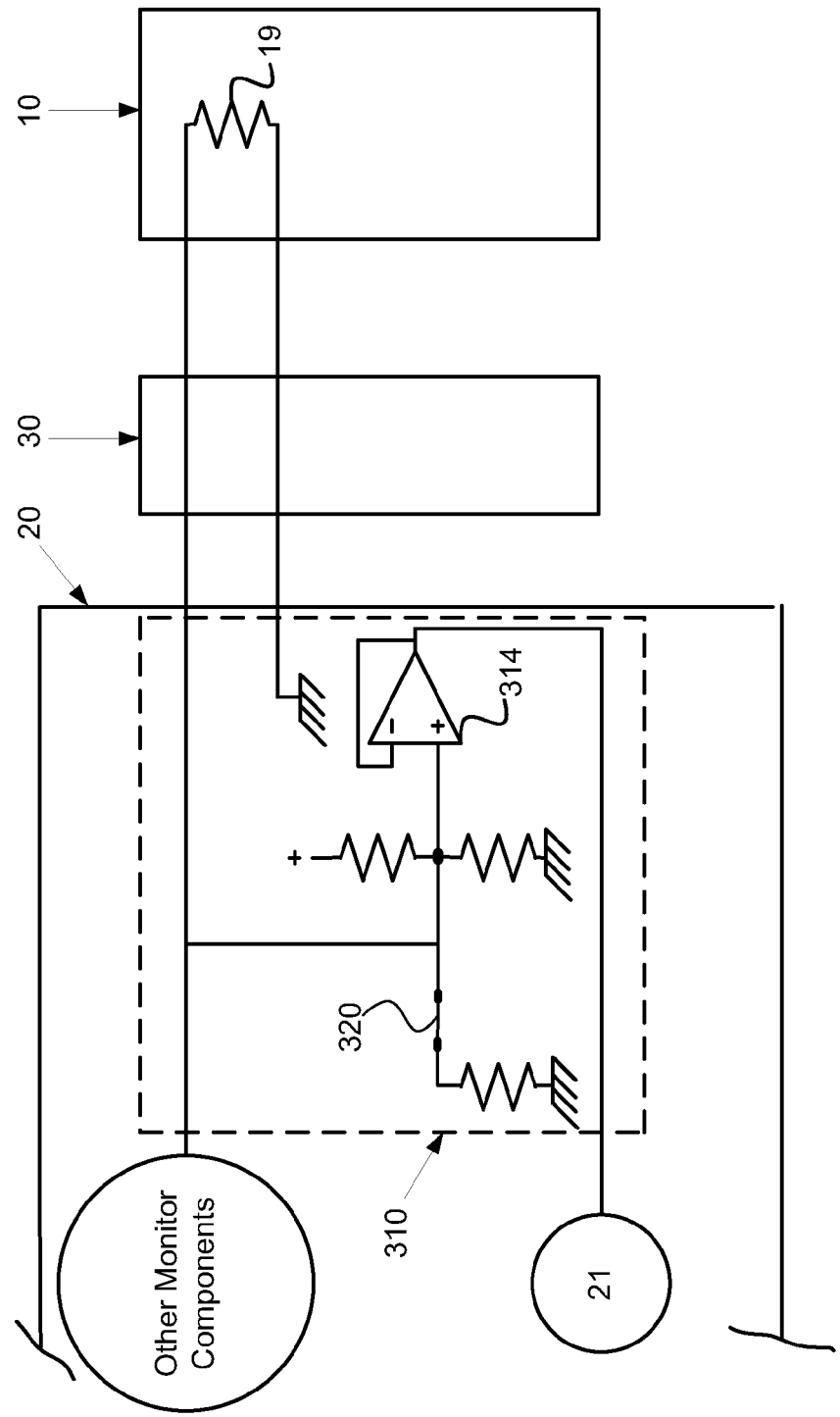

FIGS. 3A and 3B illustrate one embodiment of an identification/calibration test circuit that provides for a redundancy testing of the circuit to ensure that proper sensor identification is achieved. The identification element test subsystem 300 has a power supply 310 that in the present embodiment comprises a voltage divider having a first resistor 312 and a second resistor 314. The test subsystem 300 further includes a resistor 316 that is selectively connectable to a common junction 318 between the resisters 312, 314 of the power supply 310. A selectively actuable switch 320 is operative to move between an open position as shown in FIG. 3A and a closed position as shown in FIG. 3B. When a probe 10 is interconnected to the monitor 20 by the cable 30, the identification element 19 is interconnected to the common junction 318 of the test subsystem 300 by a first conductor 96 and grounded by a second conductor 94, such that an interrogation signal (e.g., a voltage) may be applied across the identification element 19.

Measurement of the voltage level at the common junction 316 may be effectuated by any appropriate measurement device. For instance, the input of a non-inverting buffer amplifier 322 may be interconnected to the common junction 316. The output of the buffer amplifier 322 may be interconnected to the processor 21 of the monitor 20. As will be appreciated, the response of the common junction 318 is the same as the response at the input of the buffer amplifier 322. In this regard, measurement of the voltage at the common junction 318 provides measurement information that represents the effect of the identification element 19 on the test subsystem 300. For instance, if the applied voltage of the power source 310 and the resistive values of the resistors (312, 318 and, when actuated, resistor 316) are known, the one or more electrical characteristics of the identification element 19 may be derived. Accordingly, this information may be used for probe identification and/or calibration purposes.

Operation of the subsystem 300 (e.g., when probe 10 is interconnected to the monitor 20) is performed in a two-step process as shown in a first step in FIG. 3A and in a second step as shown in FIG. 3B. In a first step, the voltage of the common junction 318 is measured with the probe 10 attached and the switch 320 open. Once a first measurement is taken, the switch 320 is closed such that resistor 316 is connected to and affects the test subsystem 300 (i.e., affects the voltage seen at the common junction 318). A second measurement is then taken while the switch 320 is closed.

The use of the selectively actuable switch 320 and resistor 316 ensures that as at least two output values may be obtained for an attached probe. Further, it will be noted that the interrogation signal may be varied to allow for additional data to be obtained. For instance, an interrogation signal of two different voltages may be applied when the switch 320 is open and when the switch 320 is closed to produce four output measurements. In any case, the voltages observed at the buffer 322 may be converted, e.g., via an analog-to-digital converter, and utilized by the processor to identify probe 10 characteristics (e.g., a resistance value of the identification element 19, which may be correlated to one or more calibration values). The test subsystem 300 provides a simple apparatus wherein one interrogation signal can produce two separate outputs for identification and/or calibration of an attached probe.

Figure 4:
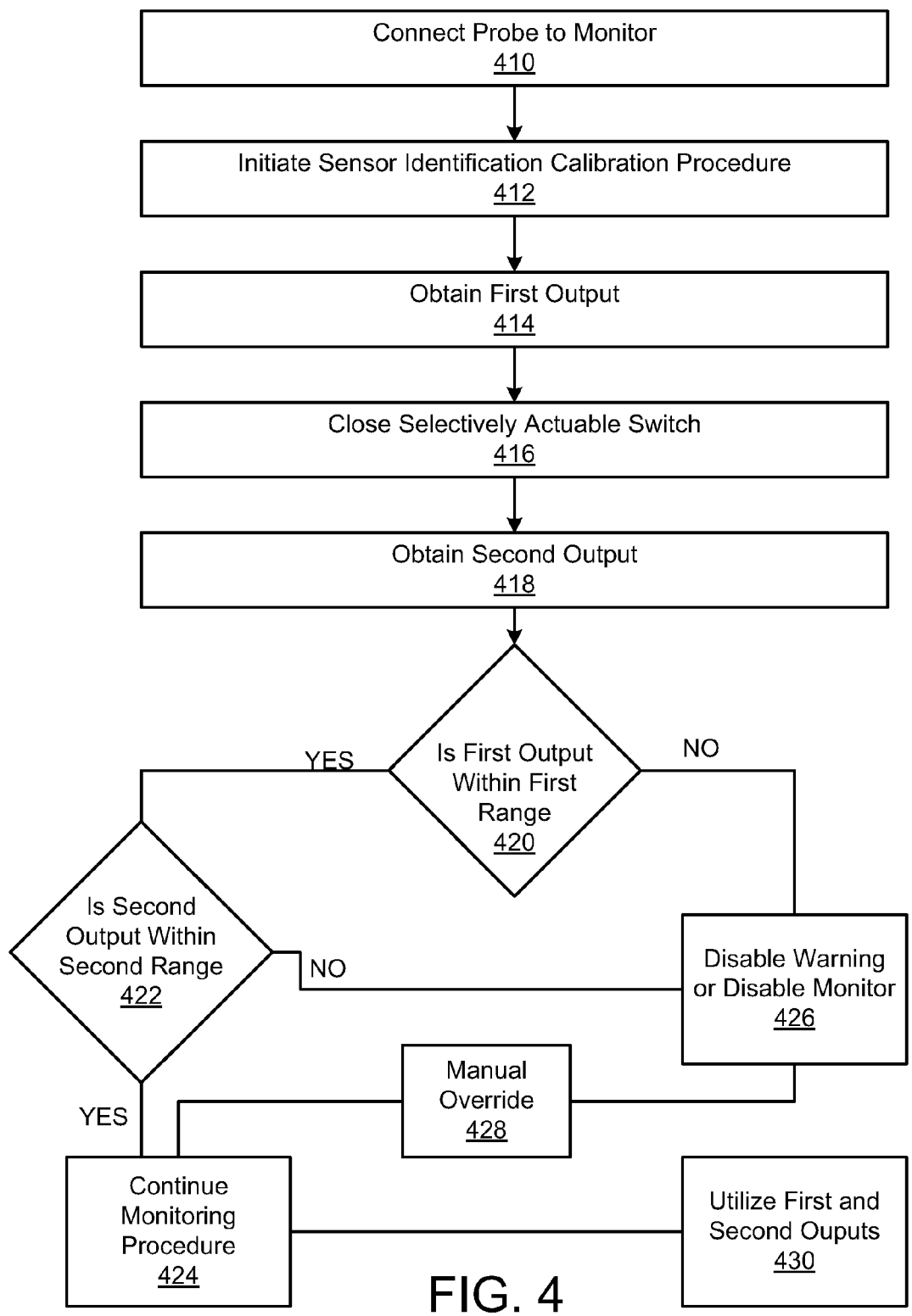
FIG. 4 is a flow chart illustrating a process implemented in connection with the circuit of FIGS. 3A and 3B.

The photoplethysmographic monitor 20 may be provided with pre-programmed or preset process functions to utilize the outputs from the test subsystem 300. Referring to FIG. 4, an exemplary process 400 is described. Initially, a probe 10 is interconnected (410) probe to the monitor 20. A probe information procedure is initiated (412). This procedure may be initiated (412) automatically by the monitor 20 upon an electrical circuit being completed by the identification element 19. Alternatively, the probe information procedure may be initiated (412) by a user via interface with user control panel 25 of monitor 20, e.g., upon prompting by display 24 of monitor 20. In any case, monitor 20 may be pre-programmed so that the probe information procedure must be completed or manually overridden by a user before photoplethysmographic patient monitoring of blood analyte concentration, etc. can proceed.

Upon initiation of the probe information procedures, monitor 20 may automatically obtain (414) a first output from the test subsystem 300 that corresponds to the application of a first interrogation signal (e.g., voltage) when the identification element 19 is electrically attached to the test subsystem 300. The switch 320 may then be closed (416) in order to add resistor 316 to the circuit of the test subsystem 310. A second output may then be obtained (418), which corresponds to the first interrogation signal when the identification element 19 and resistor 316 are electrically attached to the test subsystem 300.

Upon obtainment of the first and second output values, processor 21 of monitor 20 may determine whether the value extracted from the first output is within a first predetermined range (step 420). By way of example, a voltage associated with the first output may be compared with a predetermined voltage range wherein a value within the range indicates that a known, compatible probe (i.e., probe 10) is interconnected to the monitor 20. Next, the processor 21 of the monitor 20 may determine if the second output is within a second predetermined range (step 422). By way of example, a voltage associated with the second output may be compared with a predetermined voltage range to confirm the probe is a known, compatible probe. In this regard, if both outputs are within their respective predetermined ranges, the processor 21 may automatically provide for continuation of photoplethysmographic monitoring procedure (step 424), wherein one or more blood analyte concentration levels are determined by probe 10 and the monitor 20. Alternatively, processor 21 may provide an output to a user (e.g., at display 24) indicating that a compatible probe (i.e., probe 10) has been detected and prompt the user to provide an input at user control panel 25 to initiate photoplethysmographic monitoring procedures. In conjunction with blood analyte concentration determinations, the first and second output values may be utilized alone or in combination to select appropriate calibration values for probe 10 (step 430).

In the event that the first, second or both information output values are outside of the corresponding predetermined range, processor 21 may be pre-programmed to disable monitor 20 from continuing a photoplethysmographic monitoring procedure (step 426). Such disablement may be accompanied by a corresponding output at display 24, indicating to the user that an inappropriate or incompatible probe has been interconnected to the monitor 20. Alternatively, a warning signal may be output to a user at display 24, whereupon processor 21 may be pre-programmed to allow a user enter a manual override (428) input at the user control panel 25 and continue photoplethysmographic monitoring procedures (step 424).

Referring again to FIGS. 3A and 3B, it will be noted that the testing subsystem 300 may also be utilized to test other components of the monitor 20. Such testing may be performed to set or otherwise account for gain and/or offset errors of the monitor 20. In this regard, the common junction 318 of the testing means 310 may be interconnected to various components of the monitor 20 in order to obtain first and second output/responses for those components in view of an applied interrogation signal (e.g., voltage). Again, these first and second responses may be utilized to derive information relating to the attached component. That is, as the voltage of the power source 310 (e.g., interrogation signal) and the value of the resistors 312, 314 and 316 are known values, the effects of the attached monitor component on the resulting circuit may be derived. That is, two equations having two unknown values may be simultaneously solved to generate information that is specific to the attached monitor component. This monitor component specific information may be correlated with known values for the component to determine if the component is within acceptable limits and/or if adjustments to the component and/or monitor calculations should be made. Two monitor components that may be tested using the testing subsystem 300 are an amplifier and analog-to-digital converter of the detection module of the monitor 20

During operation of the monitor 20 and attached sensor 10, analog signals from the photodetector 18, which correspond to light signals from the LEDs 12, 14, are received by the detection circuit 23 and converted to digital signals utilizing an analog-to-digital converter. In conjunction with such conversion, the signals may be amplified by an amplifier. These digital signals are then provided to the processor 21 and a blood analyte module 40 for further processing. Prior to obtaining measurements from the photodetector 18 and LEDs 12, 14 it may be desirable to calibrate the detection circuit 23. In this regard, the gain and/or offset of the analog-to-digital converter and/or amplifier may be tested by the test subsystem 300 to determine their current operating conditions. For instance, amplifier may be interconnected to the common junction 318 of the test subsystem 300. As with the identification element 19, first and second voltage measurements of common junction 318 may be made with the switch 320 opened and closed, while the amplifier is electrically connected to the test subsystem 300. Again, as the voltage of the power source 310 and the value of the resistors 312, 314 and 316 are known, the effects of the amplifier on the circuit may be determined and one or more amplifier specific values may be derived. These amplifier specific values may be correlated with known values to determine if the gain of the amplifier is acceptable/correct. Accordingly, appropriate adjustment to the amplifier may then be made. A similar process may be performed for other components of the detection circuit 23 (e.g., an analog digital converter) and/or for other components of the monitor 20. Likewise, other sensor based components (e.g., LEDs, photodiodes, etc.) may also be tested utilizing the test subsystem. As will be appreciated, use of the testing means to test other monitor/sensor components may require one or more additional selectively actuable switches for selectively connecting such components to the testing subsystem 300.

Photodetector Circuit Fault Detection

Figure 5:
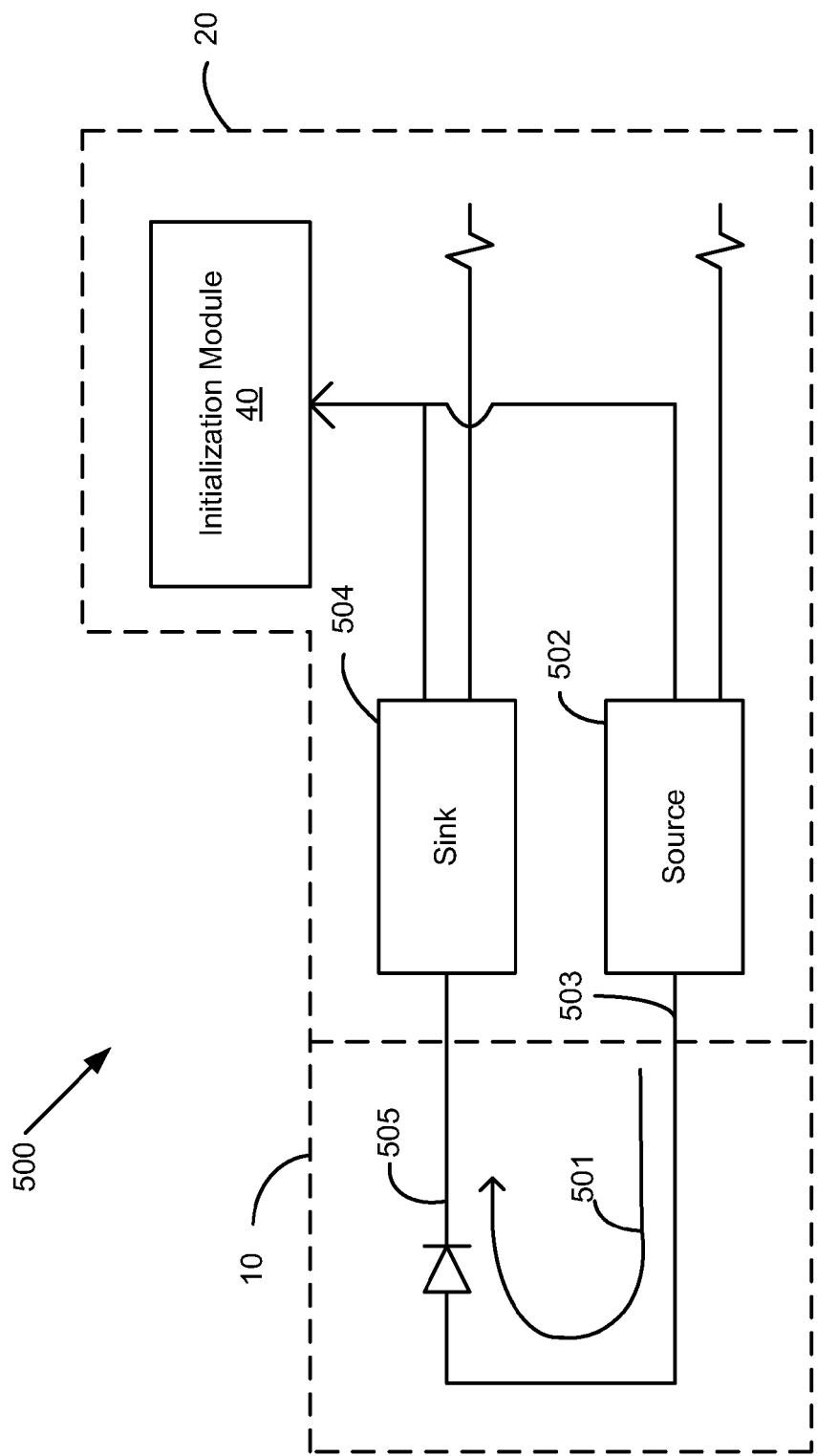
FIG. 5 illustrates a photodetector circuit for use in the system of FIG. 1.

As noted above, it is desirable to obtain initialization information regarding a number of probe components. FIG. 5 illustrates a subsystem 500 for obtaining initialization information regarding the photodetector 18 of the probe 10. In this regard, a photodetector circuit may or may not be configured to provide probe identification, calibration or other information. Accordingly, the initialization information may include encoded information for probe identification, calibration and the like, or may simply be values for use in probe fault detection. In the illustrated embodiment, the subsystem 500 is useful for identifying potential probe faults relating to the photodetector circuit of the probe 10.

The photodetector 18 generates an electrical current, generally indicated by the reference numeral 501, in response to an optical signal incident on the photodetector 18. In the illustrated circuit, this current will generally be substantially identical at the input 503 and output 505 leads of the probe 10, in the absence of any faults such as shorts or opens. Accordingly, the illustrated subsystem includes an input module 502 for monitoring the signal drawn by the photodetector circuit and a sink module 504 for monitoring the output signal from the photodetector circuit. Each of the modules 502 and 504 includes a signal detector and an A/D converter, for example, an oversampling A/D converter as described above having a frequency of 40-50 kHz. The resulting digital signals from the modules 502 and 504 are provided to the initialization module 40 which compares the signals to identify any potential faults.

A variety of different kinds of comparisons may be implemented by the module 40 to identify potential faults. For example, charge corresponding to a single pulse of the optical signal may be integrated at each of the modules 502 and 504 to obtain integrated values that can then be matched (e.g., to within a defined error threshold) to identify potential faults. In the illustrated embodiment, the modules 502 and 504 are associated with oversampling A/D converters that enable the module 40 to track the optical signal pulse waveform (as represented in the corresponding electrical signals). This allows for use of any of a variety of waveform parameters, or combinations thereof, for improved detection of potential faults.

In this regard, FIG. 6A shows input 600 and output 602 signal portions corresponding to a fault-free photodetector circuit, whereas FIG. 6B illustrates an example of input 604 and output 606 signal portions that may indicate a probe fault. It will be appreciated that the polarities or amplitudes of the detected input and output signals may vary for certain detection circuit implementations, but the waveforms should generally correspond when no faults are present. Thus, illustrated signals 600 and 602 generally correspond whereas signals 604 and 606 do not. Such correspondence may be determined by module 40 by reference to parameters such as: the number and location of maxima, inflection points, zero (reference) crossings or the like; peak values; area under a pulse; pulse duration; etc. for example, the module 40 may monitor pulse duration and amplitude at a center portion of the pulse to detect potential faults. That is, if the pulse durations and center amplitude values of the input and output signals do not match to within empirically established limits, a potential fault is indicated and that probe may be locked out from operating with the monitor and an appropriate error message may be displayed.

Figure 7:
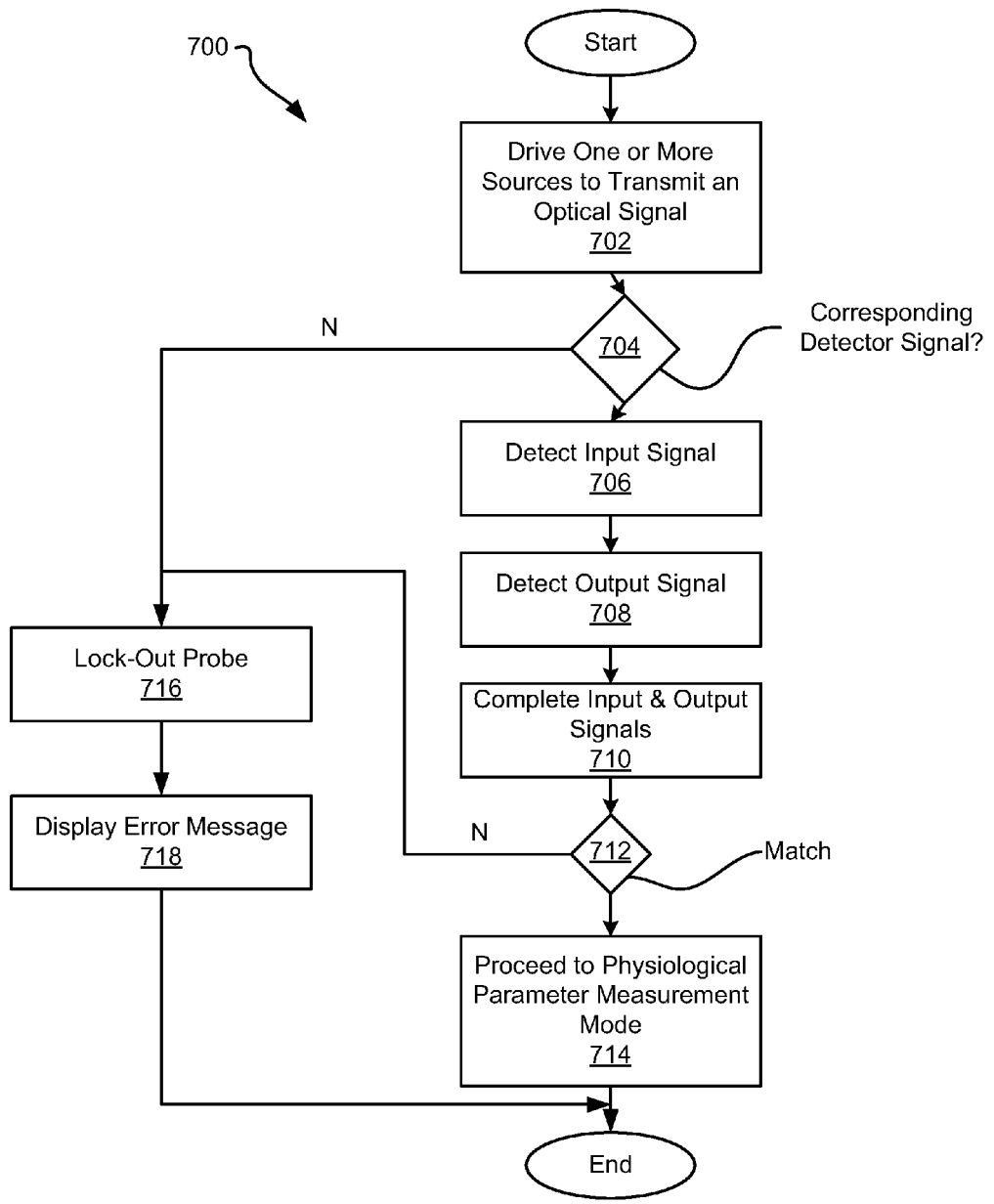
FIG. 7 is a flow chart illustrating an initialization process that may be implemented in connection with the circuit of FIG. 5.

A corresponding process 700 may be summarized by reference to the flowchart of FIG. 7. The illustrated process 700 is initiated by driving (702) one or more of the sources to provide an optical signal. That is, the red and/or infrared LEDs may be driven to provide a signal that will cause the photodetector to generate an electrical output if the photodetector is functioning properly. In this regard, the optical signal may be transmitted as part of a dedicated initialization process or an initialization routine may be run during normal operation of the pulse oximeter using optical signals transmitted for the purpose of measuring a physiological parameter of the patient. The input and/or output module may then be operated to determine if a corresponding detector signal has been received (704). For example, in certain cases, a malfunctioning probe may draw no current and provide no output corresponding to an optical signal incident on the probe. In such cases, the probe may be locked out (716) (that is, the monitor may be controlled to prevent operation of the probe) and an appropriate error message may be displayed (718) on the monitor.

If there is a detector signal, the input and output signals may be detected (706 and 708) and compared (710) to determine whether the signals match. If the signals match (712) then no probe fault condition is detected and the monitor may proceed (714) to or continue in the physiological parameter measurement mode. Otherwise, the probe is locked out (716) and an appropriate error message is displayed (718) on the monitor.

Adaptive Source Circuit Fault Detection

As described above, the initialization module 40 of the illustrated embodiment is operative to execute separate initialization processes, e.g., fault detection processes, relative to the identification/calibration circuit and the photodetector circuit. The module 40 may also be operative to obtain initialization information concerning one or more of the sources, e.g., the red and/or infrared LED. A variety of different types of initialization information may be obtained in this regard. The discussion below provides the example of interrogating the probe source circuits for the purposes of fault detection.

Figure 8:
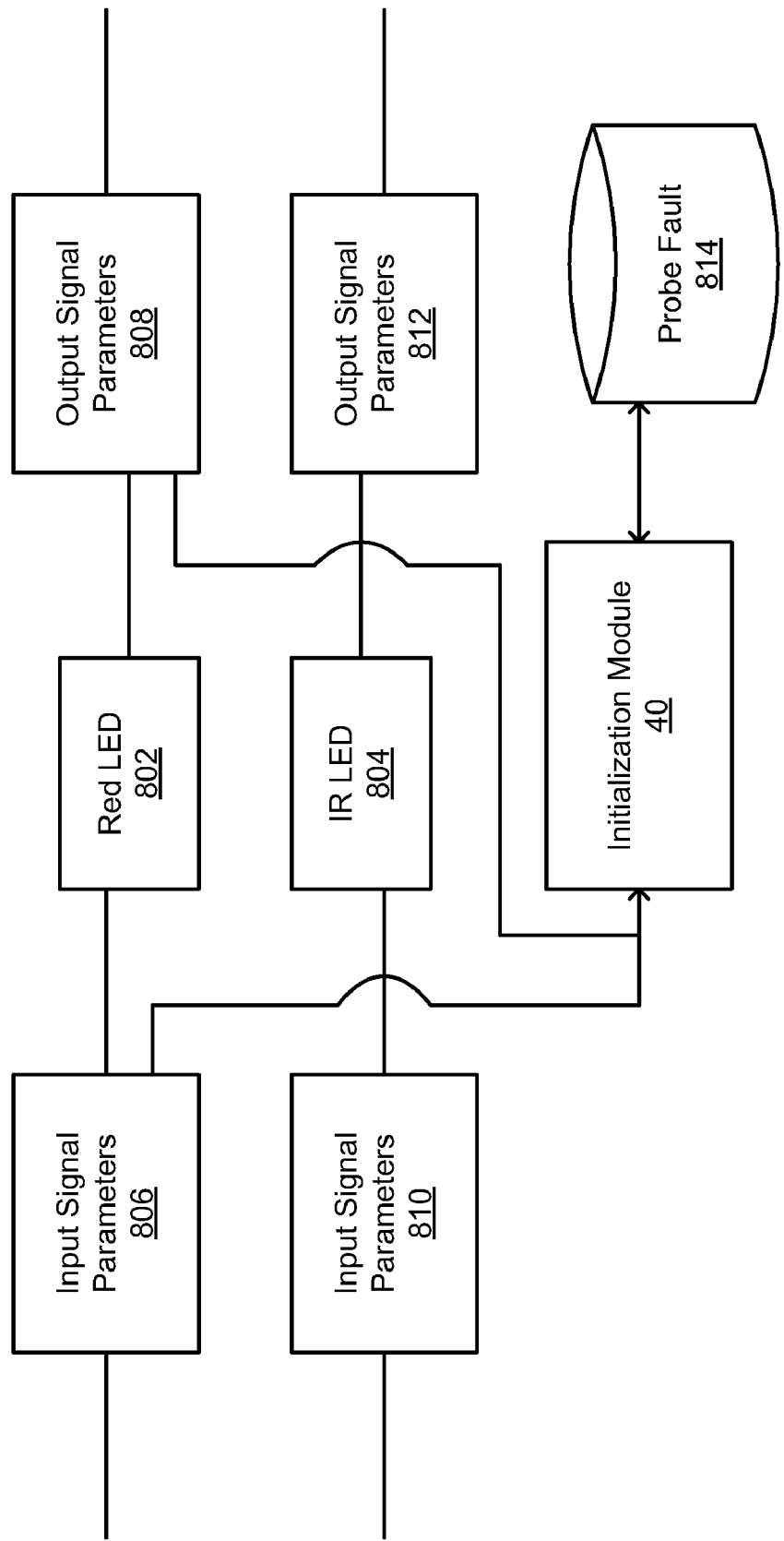
FIG. 8 illustrates source circuits for use in the system of FIG. 1.

FIG. 8 illustrates a source circuit fault detection subsystem 800. The subsystem 800 is operative for identifying potential faults, such as shorts or opens, with respect to the circuits for driving the sources 802 and 804. Conventionally, a probe source has been tested for potential faults by measuring a fault parameter, such as a voltage drop across the source, and comparing that fault parameter to a range of acceptable values. However, it has been recognized that such a static comparison may be insufficient due to certain operational variations such as changes in probes or probe types and changes in the drive signal, e.g., associated with different probe types or patient variations.

Accordingly, the illustrated subsystem 800 implements an adaptive algorithm in this regard. The illustrated subsystem 800 includes input signal parameter measurement modules 806 and 810 and output signal parameter modules 808 and 812 associated with the sources 802 and 804 respectively. Each of the modules 806, 808, 810 and 812 measures one or more parameters associated with the relevant signal such as current and/or voltage or derived parameters such as power. These measured values are provided to the initialization module 40 which calculates corresponding fault parameter values. For example, the fault parameter values may include one or more of the voltage drop across a source, the power drop across a source, and the degree of match between the input and output current. This determined fault parameter value is then compared to a valid range or a fault threshold or range for the relevant operational conditions. For example, the valid values or fault values may be accessed from storage 814 where the values are indexed to particular probe types or drive settings. Alternatively, the valid values or fault values may be determined based on an algorithm that reflects probe types or drive settings.

Figure 9:
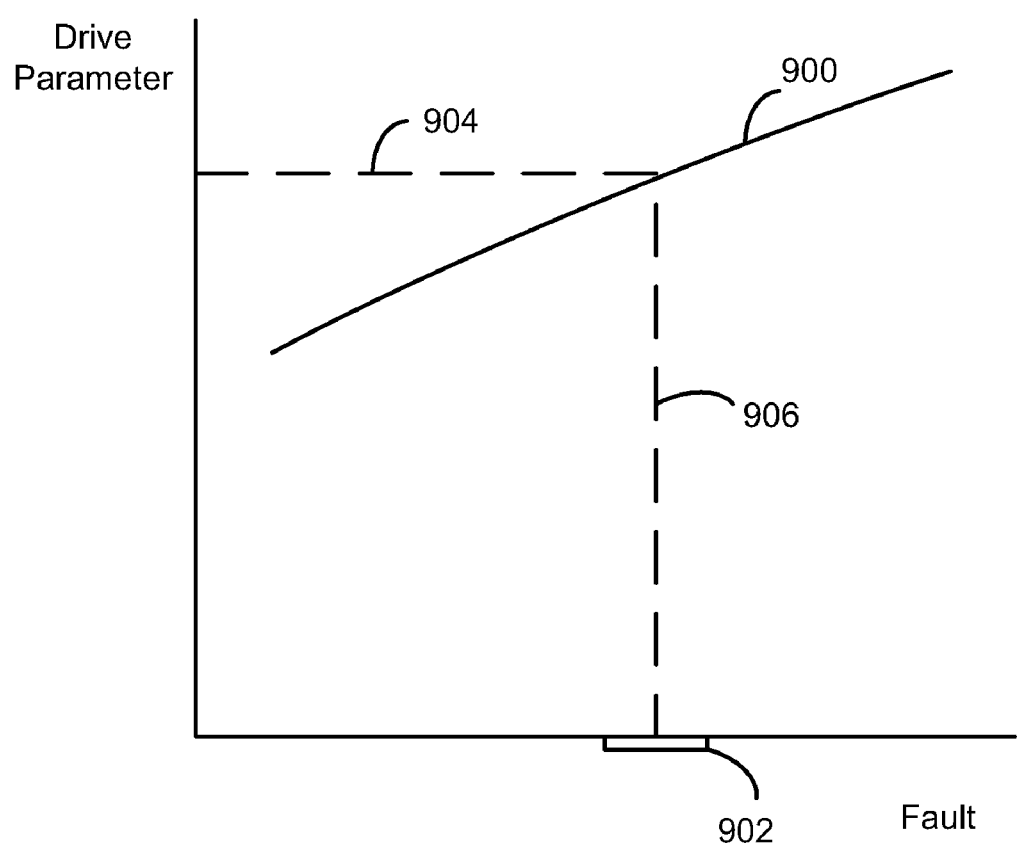
FIG. 9 graphically illustrates a process for defining an adaptive fault parameter window that may be implemented in connection with the circuit of FIG. 8.

In this regard, an adaptive window may be defined for use in detecting potential probe fault conditions. This is graphically illustrated in FIG. 9. In FIG. 9, a particular drive parameter such as, for example, the drive voltage or drive current is plotted against the expected corresponding fault parameter such as, for example, a voltage drop across the source. It will be appreciated that multiple parameters may be utilized in practice and that curves such as shown in FIG. 9 may be provided for a variety of probe types or other variations in operational conditions. As shown, the plot defines a curve 900 reflecting the observation that fault parameters may vary as a function of the drive parameters. In the illustrated example, an adaptive or movable window 902 of valid fault parameter values is defined depending on the measured drive parameter value 904. That is, a given drive parameter value 904 is expected to correspond to a particular fault parameter value 906 under the relevant operational conditions. The window 902 is empirically defined to define valid fault parameter value limits around the fault parameter value 906. It will be appreciated that this window 902 moves as a function of the drive parameter value.

Figure 10:
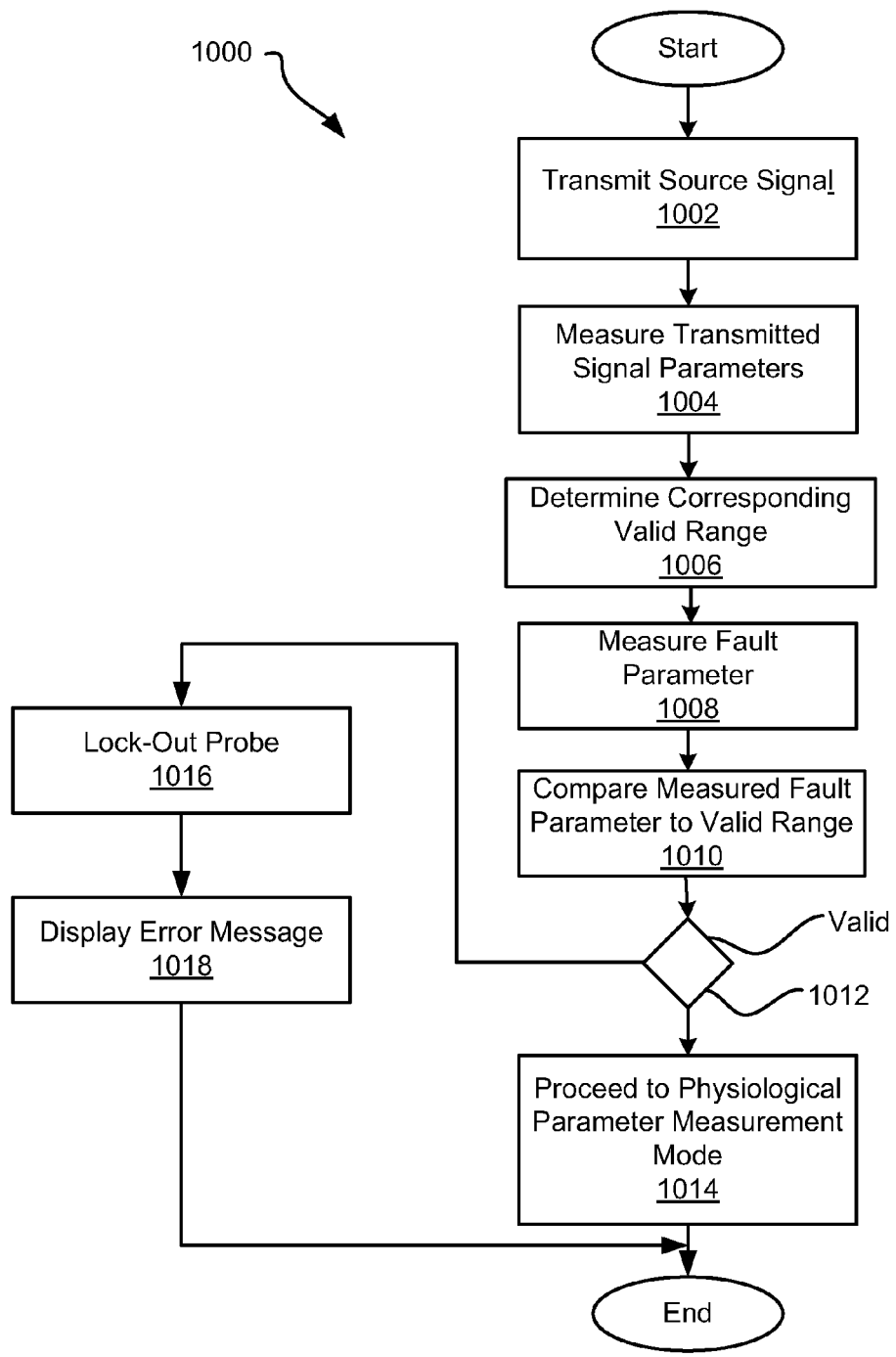
FIG. 10 is a flow chart illustrating an initialization process that may be implemented in connection with the circuit of FIG. 8.

A corresponding process 1000 may be summarized by reference to the flow chart of FIG. 10. The illustrated process 1000 is initiated by transmitting (1002) a source drive signal relative to the red and/or infrared LED. This signal may be a dedicated signal transmitted as part of an initialization process or may be a signal that is transmitted for the purpose of measuring a physiological parameter of a patient. The transmitted signal parameters are then measured (1004). As noted above, these parameters may include the signal voltage, signal current, derived values such as power, or other signal parameter values. A corresponding valid range for the fault parameter is then determined (1006). As discussed above, this may involve defining an adaptive window of valid fault parameter values as a function of a signal drive parameter. It will be appreciated that the drive value may be measured or may be determined from a selected setting.

The desired fault parameter is then measured (1008) and/or derived. For example, a signal voltage, current or other value may be measured at a source output. These values may be used in conjunction with corresponding input signal values to determine a voltage drop or other drive related value such as a power drop that can be used as a fault parameter. The measured fault parameter is then compared (1010) to the valid range defined as described above. If the fault parameter value is within the valid range (1012) then no fault condition is identified and the monitor may proceed (1014) to or continue in the physiological parameter measurement mode. Otherwise, the probe is locked out (1016) and an appropriate error message is displayed (1018) on the monitor.

While various embodiments of the present invention have been described in detail, it is apparent that further modifications and adaptations of the invention will occur to those skilled in the art. However, it is to be expressly understood that such modifications and adaptations are within the spirit and scope of the present invention.

What is claimed:

1. A method for use in a pulse oximeter, comprising the steps of:
   providing a photoactive element for providing electrical signals responsive to optical signals incident thereon;
   applying an optical signal to said photoactive element;
   detecting a first signal associated with an input lead of said photoactive element; and
   detecting a second signal associated with an output lead of said photoactive element; and
   analyzing said detected first and second signals to obtain information regarding said photoactive element for use in controlling operation of said pulse oximeter in connection with a probe including said photoactive element.

2. The method of claim 1, wherein said first and second signals comprise an input current to said photoactive element and an output current from said photoactive element, respectively.

3. The method of claim 1, wherein analyzing comprises comparing said first and second signals to obtain said information.

4. The method of claim 3, wherein said comparing comprises comparing at least a first parameter of said first signal with at least a first corresponding parameter of said second signals.

5. The method of claim 4, wherein said at least a first parameter comprises at least one of:
   amplitudes of said signals;
   maxima of said signals;
   inflection points of said signals;
   reference crossings of said signals; and
   pulse waveforms of said signals.

6. The method of claim 1, wherein analyzing said detected electrical signal to obtain information comprises obtaining information relating to at least one of:
   initialization information; and
   fault information for use in determining probe fault conditions.

7. The method of claim 6, further comprising utilizing said initialization information for at least one of:
   probe identification; and
   selection of calibration information for use in calibrating at least one of said pulse oximeter and said probe for subsequent operation.

8. An apparatus for use in a pulse oximeter comprising:
   at least one source for generating optical signals;
   a photoactive element for providing electrical signals responsive to optical signals incident thereon;
   an input module for measuring an input signal drawn into said photoactive element in response to said optical signals; and
   an output module for measuring an output signal output from said photoactive element in response to said optical signals.

9. The apparatus of claim 8, further comprising;
   a processor operatively interconnected to said input module and said output modules, wherein said processor is operative to receive measurements of said input and output signals from said input and output modules, respectively.

10. The apparatus of claim 9, wherein said processor is operative to compare said measurements to obtain information relating to at least one of:
    identification information relating to said photoactive element;
    calibration information for calibrating said pulse oximeter; and
    fault information for use in determining fault conditions associated with said photoactive element.

11. The apparatus of claim 9, wherein said input module and said output module each comprises an A/D converter.

12. The apparatus of claim 11, wherein said processor is operative to receive outputs from each said A/D converter and track optical signal pulse waveforms into and out of said photoactive element.

13. The apparatus of claim 12, wherein said processor is operative to compare an input optical pulse waveform to an output optical pulse waveform.

14. The apparatus of claim 8, wherein said input and output modules are releaseably interconnected to said photoactive element.

* * * * *